United States Patent [19]

Naujoks et al.

[11] Patent Number: 5,071,744

[45] Date of Patent: Dec. 10, 1991

[54] PROCESS AND MONOCLONAL ANTIBODY FOR THE SPECIFIC DETERMINATION OF PANCREATIC α-AMYLASE IN THE PRESENCE OF SALIVARY α-AMYLASE

[75] Inventors: Kurt Naujoks, Gauting; Karl Wulff, Weilheim; Martin Gerber, Weilheim-Unterhausen, all of Fed. Rep. of Germany

[73] Assignee: Boehringer Mannheim GmbH, Mannheim, Fed. Rep. of Germany

[21] Appl. No.: 595,680

[22] Filed: Oct. 9, 1990

Related U.S. Application Data

[63] Continuation of Ser. No. 327,361, Mar. 23, 1989, abandoned, which is a continuation of Ser. No. 815,410, Dec. 31, 1985, abandoned.

[30] Foreign Application Priority Data

Jan. 9, 1985 [DE] Fed. Rep. of Germany ....... 3500526

[51] Int. Cl.$^5$ ................. G01N 33/536; G01N 33/543; C12Q 1/40; C12P 21/08
[52] U.S. Cl. ...................................... 435/7.4; 435/7.1; 435/7.6; 435/7.92; 435/22; 435/70.21; 435/172.2; 435/240.26; 435/975; 436/518; 436/548; 530/808; 530/809; 935/106; 935/108
[58] Field of Search .................. 435/7.1, 7.6, 7.92, 435/22, 70.21, 106, 108, 110, 172.2, 240.26, 975; 436/518, 548, 808, 809; 530/808, 809

[56] References Cited

U.S. PATENT DOCUMENTS

| 4,474,892 | 10/1984 | Murad et al. | 436/828 |
| 4,939,082 | 7/1990 | Naujoks et al. | 435/7 |
| 4,945,043 | 7/1990 | Gerber | 435/7 |

FOREIGN PATENT DOCUMENTS

8183098 10/1983 Japan .

OTHER PUBLICATIONS

Patent Abstracts of Japan, Fractionation and Determination of Isozyme, vol. 8, No. 15 (C-206) (1452) 1/21/84, Sakata.
European Patent Applic 85300991.8, published Aug. 21, 1985.
Hagele et al., (1982) Clinical Chemistry, vol. 28, No. 11, pp. 2201-2205.
Derwent Publication Ltd., #C83118652 (1983).
Goding, (1980) Journal of Immunological Methods, vol. 39, pp. 285-308.
Whitlow et al., (1979) Clinical Chemistry, vol. 25, No. 3, pp. 481-483.
Chemical Abstracts (1984), vol. 100, No. 11, p. 241, item #82015d.

*Primary Examiner*—David M. Naff
*Attorney, Agent, or Firm*—Felfe & Lynch

[57] ABSTRACT

Pancreatic α-amylase is determined in body fluid in the presence of salivary α-amylase by combining the body fluid with a monoclonal antibody that inhibits salivary α-amylase by 95% or more and inhibits pancreatic α-amylase by 50% or less, and then detecting pancreatic α-amylase with a system for the detection of α-amylase. The monoclonal antibody may be in immobilized form. The monoclonal antibody is preferably produced by immunizing a Balb/c mouse or an AJ mouse with a specific immunogen for a specific number of times, fusing β-lymphocytes obtained from the mouse with a myeloma cell line to form an antibody producing hybridoma cell line, cloning and screening the hybridoma cell line for the desired monoclonal antibody, and isolating the monoclonal antibody. The immunogen contains modified or unmodified salivary α-amylase, aluminum hydroxide and *Bortadella pertussis*.

20 Claims, No Drawings

PROCESS AND MONOCLONAL ANTIBODY FOR THE SPECIFIC DETERMINATION OF PANCREATIC α-AMYLASE IN THE PRESENCE OF SALIVARY α-AMYLASE

This application is a continuation of application Ser. No. 327,361, filed Mar. 23, 1989, now abandoned, which is a continuation of application Ser. No. 06/815,410, filed Dec. 31, 1985, now abandoned.

The present invention is concerned with a process and reagent for the specific determination of pancreatic α-amylase in the presence of salivary α-amylase.

α-Amylase (E.C. 3.2.1.1) breaks down 1,4-d-glucosidically linked oligo- and polysaccharides, preponderantly by random hydrolysis of the 1,4-α-glucosidic bonds, to maltose and malto-oligosaccharides. Besides its use in industrial fermentation technology, the enzyme has considerable importance in the scope of clinical analysis and diagnosis. Thus, in the case of numerous diseases, the α-amylase content in body fluids, such as serum, urine and duodenal secreta, changes considerably. However, in the body, essentially two α-amylase enzymes occur, the pancreatic enzyme and the salivary enzyme. Since only the pancreatic enzyme has diagnostic importance, the task exists analytically to differentiate these two α-amylases, in the presence of further enzymes which occur rarely and only in small amounts. The difficulty here is that the two multiple forms have a similar structure and are immunologically identical (see K. Lorentz, Laboratoriumsblatter, 32, 118/1982). For the elimination of the activity of the salivary enzyme, it is known to use adsorption on anion exchangers, inhibition by wheat protein or electrophoresis or electrofocusing. However, these processes are either unsatisfactory in their separation action or are too laborious for routine diagnosis. Of the mentioned methods, only the process described in Clin. Chem., 28/7, 1525-1527/1982 of inhibiting the enzyme of the salivary type by an inhibitor obtained from wheat germ involves an expenditure of time which is acceptable for routine diagnosis but the selectivity is unsatisfactory. Even in the case of the optimum inhibitor concentration, about 13% of the activity of the salivary type enzyme is retained, whereas the activity of the pancreatic enzyme is reduced to about 81%.

In older and non-published European Patent Application No. 84 114 172.4, it has already been proposed to determine the pancreatic α-amylase in the presence of salivary α-amylase by working in the presence of a monoclonal antibody which reacts with the salivary α-amylase and hereby displays a cross-reactivity of 5% or less with regard to the pancreatic α-amylase. With this monoclonal antibody, it is also possible, in the case of the addition of a precipitating agent, to form an insoluble complex with the salivary α-amylase which can then be separated from the solution so that only the pancreatic enzyme remains behind in the solution and can there be determined. Alternatively, it is possible to use the monoclonal antibody in immobilised form and, in this way, to separate the salivary amylase. However, in both cases, it is necessary to form an insoluble phase and to separate it from the soluble phase.

Therefore, it is an object of the present invention to overcome these disadvantages and to provide a process and a reagent which makes possible a rapid, simple and dependable determination of the pancreatic α-amylase, in the presence of α-amylase of the salivary type, in body fluids without it hereby being necessary to have to carry out a phase separation.

Thus, according to the present invention, there is provided a process for the specific determination of pancreatic α-amylase in the presence of salivary α-amylase in body fluids, especially in serum, plasma, duodenal juice or urine, by reaction with a system for the detection of α-amylase in the presence of a monoclonal antibody, which reacts with salivary α-amylase, wherein a monoclonal antibody is used which specifically inhibits the salivary enzyme but does not inhibit the pancreatic enzyme by more than 50%.

The process according to the present invention is based upon the very surprising discovery of a monoclonal antibody which inhibits the salivary enzyme but not the pancreatic enzyme. This was not to have been expected since it was known that the salivary and pancreatic enzymes are immunologically identical (see Gerhard Pfleiderer, Lab. Med., 7, 189-193; K. Lorentz, loc. cit.). Thus, M. K. Schwarz states in "Immunoassay of Enzymes—an Overview", pp. 4-9, 1983, that antibodies against salivary α-amylase inhibit the enzyme of the salivary type by 78% and the enzyme of the pancreatic type by 75%. Therefore, it was not to have been foreseen that it would be possible to develop a monoclonal antibody which would make possible a practically quantitative differentiation between the two enzymes by selective, highly specific inhibition. An inhibition of 95% and more for the salivary enzyme is thereby achieved in the case of the preferred antibodies.

The new monoclonal antibodies used for the process according to the present invention can be produced by hybridoma cell lines that have been deposited with the NCACC under the numbers (99D12) 84122003 and (89E2) 84122004 (National Collection of Animal Cell Cultures, Porton Down, Great Britain).

According to the present invention, the antibody can be obtained by immunising experimental animals with native or modified salivary α-amylase, fusion of B-lymphocytes of the immunised animals so obtained with transforming agents, cloning and culturing of the so formed hybrid cells which produce the monoclonal antibodies and isolation of the latter. Especially suitable animals for the production of the salivary α-amylase antibodies are rats and mice. Immunisation takes place either with native human salivary α-amylase or with modified salivary amylase. If native enzyme is used, then the commercially available, electrophoretically uniform preparations can be used for this purpose. Chemically modified salivary α-amylase can also be obtained by known methods of enzyme modification, such as are described, for example, in detail in Federal Republic of Germany Patent Specification No. 25 43 994. Suitable modification agents include, for example, N-bromosuccinimide (NBS) with oxidation of tryptophane groups on the protein (BBA, 143, 462-472/1967), carboxymethylation with iodoacetate (IAA), which mainly attacks on the histidine or nitration with tetranitromethane (TNM) (J. Biol. Chem., 238, 3307/1963), as well as diazotisation with diazotised sulphanilic acid (Meth. Enzymol., 25, 515-531/1972). The enzyme modified with TNM thereby proves to be the best suited in the case of the use of Balb/c mice or the native enzyme in the case of the use of AJ mice.

Immunisation takes place by the conventional administration of the native or modified enzyme, preferably in combination with an adjuvant. As adjuvant, it is preferred to use aluminium hydroxide, together with *Bordetella pertussis*.

If, for the immunisation, native salivary α-amylase is used in AJ mice or TNM-modified salivary α-amylase in Balb/c mice, then the immunisation preferably takes place over at least 9 months with at least 7 immunisations (injections i.p.).

After immunisation has taken place, the B-lymphocytes of the immunised animals are fused with transforming agents according to conventional methods. Examples of transforming agents which can be used within the scope of the present invention include myeloma cells, transforming viruses, for example Epstein-Barr virus, or the agents described in Federal Republic of Germany Patent Specification No. 32 45 665. The fusioning takes place according to the known process of Koehler and Milstein (Nature, 256, 495–497/1975). The hybrid cells hereby formed are cloned in conventional manner, for example with the use of a conventional cell sorter, and the clones obtained, which form the desired monoclonal antibodies, are cultured. On the basis of the cancer-like growth of the hybrid cells, these can be further cultured for an unlimited time and produce the desired monoclonal antibodies in any desired amount. With the monoclonal antibodies so obtained, the salivary α-amylase from body fluids can be quantitatively inhibited so that the remaining amylase activity is to be attributed to the pancreatic α-amylase.

For the determination process according to the present invention, the monoclonal antibodies can be used as such or their fragments ($F_c$ fragments) displaying corresponding immunological properties. Therefore, by the expression "monoclonal antibody" there is here also to be understood the fragments. Not only the complete antibodies but also the fragments thereof can be used in immobilised form.

Surprisingly, the monoclonal antibodies used according to the present invention display towards the pancreatic α-amylase an inhibition of 5% or less and, in many cases, an inhibition of only 1% is reached and, in some cases, even an inhibition lying below the limits of measurement. Therefore, it is suitable instead of the previously known inhibiting material obtained from wheat germ or of the binding monoclonal antibodies of the above-mentioned earlier Patent Application for the specific determination of pancreatic α-amylase in body fluids.

The determination of the α-amylase as such takes place according to the methods known for this purpose. Since the monoclonal antibodies according to the present invention selectively inhibit the α-amylase of the salivary type and thus remove it from the enzyme activity determination, the values obtained in the case of the α-amylase determination in the presence of the monoclonal antibodies correspond solely to the activity due to the pancreatic enzyme.

The process according to the present invention is preferably carried out with a system for the detection of α-amylase which comprises a maltopolyose with 4 to 7 glucose residues in the molecule, maltose phosphorylase, β-phosphoglucomutase, glucose-6-phosphate dehydrogenase and NAD.

A further system preferred in the scope of the present invention for the detection of α-amylase comprises nitrophenylmaltopolyose with 4 to 7 glucose residues in the molecule and α-glucosidase.

A further preferred detection system for α-amylase comprises starch modified with determinable groups.

The expression "modified starch" includes, for example, starch which is modified with determinable groups, for example the product of Pharmacia, Sweden, commercially available under the designation "Phadebas", as well as the product described in Federal Republic of Germany Patent Specification No. 28 12 154 and also starch which has been modified in its breakdown behaviour, for example carboxymethylstarch and boundary dextrin. All these systems are known and, therefore, do not here require a more detailed description.

For carrying out the process according to the present invention, the sample fluid is preferably incubated with the antibody according to the present invention and thereafter used directly in a conventional amylase test. The period of the incubation time depends upon the activity of the antibody used and is preferably from 15 to 30 minutes.

Insofar as a separation of the salivary α-amylase appears to be desirable, the monoclonal antibody can be present not only in complete form but also in the form of fragments and also fixed on to solid carriers, for example on to immunosorptive paper or on the surface of synthetic resin tubes or pipes. In this way, the α-amylase of the salivary type is bound to the carrier, i.e. to the solid phase.

It is also possible to use a monoclonal antibody preparation which is mixed from the inhibiting monoclonal antibodies according to the present invention which are produced by several different clones.

The present invention also provides a reagent for the specific determination of pancreatic α-amylase in the presence of salivary α-amylase in body fluids, especially in serum, duodenal juices, plasma or urine, comprising a system for the detection of α-amylase and a monoclonal antibody against salivary α-amylase, wherein it contains a monoclonal antibody which specifically inhibits the salivary enzyme but does not inhibit the pancreatic enzyme by more than 50% (cross reactivity $\leq 50\%$).

With regard to the system for the detection of α-amylase contained in the reagent according to the present invention, as well as the other conditions, the statements made above in connection with the process apply correspondingly.

The present invention makes possible a simple and rapid determination of pancreatic α-amylase, in the presence of α-amylase of the salivary type, in body fluids with high specificity and thus improves the possibilities of clinical diagnosis.

The following examples are given for the purpose of illustrating the present invention:

EXAMPLE 1

A) AJ mice are immunised with 100 μg. human salivary amylase in aluminium hydroxide with *Bordetella pertussis*. In an about eight week rhythm, the animals are further immunised three or four times with, in each case, 50 μg. human salivary amylase in the same adjuvant. 4 days before fusion, the last immunisation is carried out intravenously with 50 μg. salivary amylase in physiological saline.

B) Balb/c mice are immunised with 100 μg. human TNM-modified salivary amylase in aluminium hydroxide with *Bordetella pertussis*. In an about eight week rhythm, further immunisation is carried out three or four times with, in each case, 50 μg. human TNM salivary amylase in the same adjuvant. 4 days before fusion, the last immunisation is carried out intravenously with 50 μg. of salivary amylase in physiological saline.

C) The fusion of the spleen cells with Ag8.653 (ATCC CRL 1580) or SP2/0 (ATCC CRL 1581) myeloma cells is carried out according to the standard process described in J. of Imm. Meth., 39, 285–308. The fusion ratio of spleen to myeloma cells is 5:1. The fusion products are seeded on to 20 24-culture dishes (Costar) and fed with $5 \times 10^4$ peritoneal exudate cells per culture cup. Positive primary cultures (see Example 3) are, 3 to 4 weeks after fusion, cloned with the help of a fluorescent-activated cell sorter. The cells are placed individually in 96-Costar plates and fed with $2 \times 10^4$ peritoneal exudate cells. As culture medium there is used a commercially available RPMI 1640 medium with 10% foetal calf serum (described in J.A.M.A., 199, 519/1957).

EXAMPLE 2

Modification of α-amylase with tetranitromethane (TNM)

5.2 mg. human saliva amylase (Sigma) are dissolved in 1.6 ml. tris buffer (90 mM tris HCl, 1 mM calcium chloride; pH 8.0). While stirring, 10 μl. of a 10% v/v solution of tetranitromethane (Roth) in absolute ethanol are added thereto. The mixture is left to stand for 12 hours at ambient temperature. The protein is then freed from excess tetranitromethane by dialysing overnight against the above-mentioned buffer. An extinction measurement at 381 nm showed 2.6 nitro groups per molecule of α-amylase.

EXAMPLE 3

In order to ascertain the concentration and specificity of amylase-inhibiting antibody in the serum of immunised mice or in the culture supernatant of the hybrid cells or in ascites, there is used an amylase inhibition test as screening assay.

For this purpose, in a 96-Elisa plate (Nunc) are placed 50 μl. of pancreas and salivary amylase (about 400 mU/ml.) in buffer (50 mM tris, 1% bovine serum albumin, 0.1M sodium chloride; pH 7.5) and pre-incubated with 50 μl. of the solution to be tested (for example culture supernatant) for 20 minutes.

Thereafter, the enzyme reaction is initiated with 50 μl. amylase substrate (4-nitrophenylmaltoheptaoside; Boehringer Mannheim GmbH, Order No. 56 85 89). After about 20 to 60 minutes at ambient temperature, the extinctions are determined at 405 nm in a photometer (Elisa-Reader, Kontron, Switzerland).

The following controls are also determined:
1. fresh culture medium (cf. Example 1 C))
2. culture supernatant of the clone of European Patent Application No. 84 114 172.4
3. wheat germ inhibitor (European Patent Specification No. 00 79 793), concentration 2 μg./ml. and 0.2 μg./ml.

The following results are obtained in the above-described test:

From about 4% of all primary cultures, specific salivary amylase-inhibiting activities were found, the cross-reactivity of which was less than 10%.

EXAMPLE 4

Production of ascites and determination of the activity thereof $1-2 \times 10^6$ hybrid cells (produced according to Example 1) were injected intraperitoneally into mice which had been pre-treated once or twice with, in each case, 0.5 ml. pristan (Sigma, No. T 7640). After about 15 to 20 days, 3 to 5 ml. of ascites were removed from each mouse which contained about 10 mg. IgG/ml.

In a concentration of 200 μg./ml., the monoclonal antibodies 89E2 inhibited human salivary α-amylase (800 mU/ml.) by more than 95% but human pancreatic α-amylase by less than 2% (process analogous to that described in Example 3).

We claim:
1. Process for obtaining a cell line which produces a monoclonal antibody which inhibits human salivary alpha amylase by 95% or more and inhibits human pancreatic alpha amylase by 50% or less, comprising:
   (i) immunizing a Balb/c mouse 4 or 5 times with a mixture of (a) an immunogen containing human salivary alpha amylase which has been modified by one of tetranitromethane, N-bromosuccinide, iodoacetate or diazotized sulfanilic acid, (b) aluminum hydroxide and (c) Bortadella pertussis, each immunization occurring about 8 weeks after a previous immunization,
   (ii) immunizing said mouse an additional time at least 8 weeks after the last immunization in (i) with an immunogen containing said modified human salivary alpha amylase in a physiological saline solution, and
   (iii) fusing B-lymphocytes obtained from said mouse with a transforming agent about 4 days after the immunization of (ii) to form an antibody producing cell line.
2. Process of claim 1, wherein said transforming agent is a myeloma cell line and said antibody producing cell line is a hybridoma.
3. Hybridoma cell line produced by the process of claim 2.
4. Hybridoma cell line of claim 3, wherein said hybridoma cell line is NCACC No. 84122003 or NCACC 84122004.
5. Process for obtaining a monoclonal antibody which inhibits human salivary alpha amylase by 95% or more and inhibits human pancreatic alpha amylase by 50% or less, comprising:
   (i) immunizing a Balb/c mouse 4 or 5 times with a mixture of (a) an immunogen containing human salivary alpha amylase which has been modified by one of tetranitromethane, N-bromosuccinide, iodoacetate or diazotized sulfanilic acid, (b) aluminum hydroxide and (c) Bortadella pertussis, each immu-

|  | clone 79 | Inhibition in % | | | | | |
|---|---|---|---|---|---|---|---|
|  |  | wheat germ inhibitor | | 99D12 | 99C11 | 88E8 | 89E2 |
|  |  | 2 μg./ml. | 0.2 μg./ml. |  |  |  |  |
| salivary amylase | 0 | 75 | 40 | 58 | 65 | 67 | 65 |
| pancreatic amylase | 0 | 17 | 6.2 | 1.8 | 4.6 | 0.5 | 0 | nization occurring about 8 weeks after a previous immunization, (ii) immunizing said mouse an additional time at least 8 weeks after the last incubation in (i) with an immunogen containing said modified human salivary alpha amylase in a physiological saline solution, (iii) fusing B-lymphocytes obtained from said mouse with a transforming agent about 4 days after the immunization of (ii) to form an antibody producing cell line, (iv) cloning and culturing said antibody producing cell line to produce monoclonal antibodies, (v) screening the monoclonal antibodies produced to determine those which inhibit human salivary alpha amylase by 95% or more and inhibit pancreatic alpha amylase by 50% or less, and (vi) isolating monoclonal antibodies having the properties in (v).

6. Monoclonal antibodies produced by the process of claim 5.

7. Process of claim 5, wherein said antibody producing cell line is a hybridoma selected from the group consisting of hybridoma cell line NCACC No. 84122003 and NCACC No. 84122004.

8. Monoclonal antibody produced by the hybridoma cell line of claim 7.

9. Method for the specific determination of human pancreatic alpha amylase in the presence of human salivary alpha amylase in a body fluid sample comprising reacting said body fluid sample with a monoclonal antibody produced by:

(i) immunizing a Balb/c mouse 4 or 5 times with a mixture of (a) an immunogen containing human salivary alpha amylase which has been modified by one of tetranitromethane, N-bromosuccinide, iodoacetate or diazotized sulfanilic acid, (b) aluminum hydroxide and (c) *Bortadella pertussis*, each immunization occurring about 8 weeks after a previous immunization, (ii) immunizing said mouse an additional time at least 8 weeks after the last incubation in (i) with an immunogen containing said modified human salivary alpha amylase in a physiological saline solution, (iii) fusing B-lymphocytes obtained from said mouse with a transforming agent about 4 days after the immunization of (ii) to form an antibody producing cell line, (iv) cloning and culturing said antibody producing cell line to produce monoclonal antibodies, screening the monoclonal antibodies produced to determine those which inhibit human salivary alpha amylase by 95% or more and inhibit pancreatic alpha amylase by 50% or less, and determining alpha amylase activity in said body fluid sample, wherein said alpha amylase activity is a measure of human pancreatic alpha amylase in said body fluid sample.

10. Method of claim 9, wherein said monoclonal antibody is in immobilized form.

11. Method for the specific determination of human pancreatic alpha amylase in the presence of human salivary alpha amylase in a body fluid sample comprising reacting said body fluid sample with (i) a monoclonal antibody produced by a hybridoma cell line selected from the group consisting of hybridoma cell line NCACC No. 84122003 and hybridoma cell line NCACC No. 84122004 and (ii) a system for the detection of alpha amylase, and determining alpha amylase activity in said body fluid sample, wherein said alpha amylase activity is a measure of human pancreatic alpha amylase in the body fluid sample.

12. Process for obtaining a cell line which produces a monoclonal antibody which inhibits human salivary alpha amylase by 95% or more and inhibits human pancreatic alpha amylase by 50% or less, comprising:

(i) immunizing an AJ mouse 4 or 5 times with a mixture of (a) an immunogen containing unmodified human salivary alpha amylase, (b) aluminum hydroxide and (c) *Bortadella pertussis*, each immunization occurring about 8 weeks after a previous incubation, (ii) immunizing said mouse an additional time at least 8 weeks after the last incubation in (i) with an immunogen containing said modified human salivary alpha amylase in a physiological saline solution, and (iii) fusing B-lymphocytes obtained from said mouse with a transforming agent about 4 days after the immunization of (ii) to form an antibody producing cell line.

13. Process of claim 12, wherein said transforming agent is a myeloma cell line and said antibody producing cell line is a hybridoma.

14. Hybridoma cell line produced by the process of claim 13.

15. Process for obtaining a monoclonal antibody which inhibits human salivary alpha amylase by 95% or more and inhibits human pancreatic alpha amylase by 50% or less, comprising:

(i) immunizing an AJ mouse 4 or 5 times with a mixture of (a) an immunogen containing unmodified human salivary alpha amylase, (b) aluminum hydroxide and (c) *Bortadella pertussis*, each immunization occurring about 8 weeks after a previous incubation, (ii) immunizing said mouse an additional time at least 8 weeks after the last incubation in (i) with an immunogen containing said modified human salivary alpha amylase in a physiological saline solution, (iii) fusing B-lymphocytes obtained from said mouse with a transforming agent about 4 days after the immunization of (ii) to form an antibody producing cell line, (iv) cloning and culturing said antibody producing cell lines to produce monoclonal antibodies, (v) screening the monoclonal antibodies produced to determine those which inhibit human salivary alpha amylase by 95% or more and inhibit pancreatic alpha amylase by 50% or less, and (vi) isolating monoclonal antibodies having the properties in (v).

16. Monoclonal antibodies produced by the process of claim 15.

17. Reagent useful for the specific determination of human pancreatic alpha amylase comprising:

(i) a monoclonal antibody produced by a hybridoma cell line selected from the group consisting of hybridoma cell line NCACC 84122003 and hybridoma cell line NCACC 84122004, and (ii) a system for the detection of alpha amylase.

18. Reagent of claim 17, wherein said system for the detection of alpha amylase comprises (i) a maltopolyose having from 4 to 7 glucose residues, (ii) maltose phosphorylase, (iii) β-phosphoglucomutase (iv) glucose-6-phosphate dehydrogenase, and (v) NAD.

19. Reagent of claim 17, wherein said system for the detection of alpha amylase comprises (i) a maltopolyose having from 4 to 7 glucose residues and (ii) alpha glucosidase.

20. Reagent of claim 17, wherein said system for the detection of alpha amylase comprises a starch modified by a detectable group.

* * * * *